United States Patent [19]

Hoffman et al.

[11] Patent Number: 4,806,285

[45] Date of Patent: Feb. 21, 1989

[54] HYDROGENATED GRINDELIA ACIDS AND THEIR METHYL, GLYCEROL AND PENTAERYTHRITOL ESTERS

[75] Inventors: Joseph J. Hoffman; Louis K. Hutter, both of Tucson, Ariz.

[73] Assignee: Arizona Technology Development Corp., Tucson, Ariz.

[21] Appl. No.: 116,641

[22] Filed: Nov. 4, 1987

[51] Int. Cl.[4] ............................ C09F 7/06; C09F 1/04; C09F 5/00
[52] U.S. Cl. .................... 260/104; 260/100; 260/103; 549/336
[58] Field of Search ................ 260/100, 103, 104; 549/336

[56] References Cited

U.S. PATENT DOCUMENTS 3,157,609  11/1964  McNay et al. .................... 260/97

OTHER PUBLICATIONS

Gonzalez et al., Chem. Abs. 102: 6859h (1985).
Timmermann et al., Chem. Abs. 99: 155132n (1983).
Bohlmann et al., Chem. Abs. 97: 3503e (1982).

*Primary Examiner*—Harold D. Anderson
*Assistant Examiner*—Dennis R. Daley
*Attorney, Agent, or Firm*—David G. Rosenbaum; Harry M. Weiss

[57] ABSTRACT

Novel diterpene compounds are separated from dry biomass of *Grindelia camporum*. The separated compounds are then hydrogenated and esterified. Both the hydrogenated and ester products are useful as tackifiers.

20 Claims, No Drawings

HYDROGENATED GRINDELIA ACIDS AND THEIR METHYL, GLYCEROL AND PENTAERYTHRITOL ESTERS

BACKGROUND OF THE INVENTION

The invention relates to the extraction of resins from plants.

Weil, et al., in U.S. Pat. No. 4,313,011, discloses a process for production and recovery of hydrocarbons from hydrocarbon-containing whole plants.

Weil, in U.S. Pat. No. 4,364.745, discloses a process for production and recovery of fuel gases and organic liquids from biomass by use of an upflow furnace.

Force, in U.S. Pat. No. 4,272,419, discloses treatment of styrene-butadiene rubber with saponified tall oil pitch. Force, at column 2, lines 57-61, states that in U.S. Pat. No. 3,157,609, pine tar and rosin acid soap are added with an extract of the plant Grindelia to a synthetic rubber polymer as a physical rubber softener, whereby the tack is improved in the resulting polymer.

BRIEF DESCRIPTION OF THE INVENTION

The invention provides a resin composition produced by the process, including: (a) separating resin from dry biomass of *Grindelia camporum*; (b) esterifying said resin to form esterified resin of improved oxidative stability.

The esterified resin may be hydrogenated to form hydrogenated resin of improved thermal stability.

Exemplary of the preferred thermally stable tackifier compounds of the invention are compounds of the formula I:

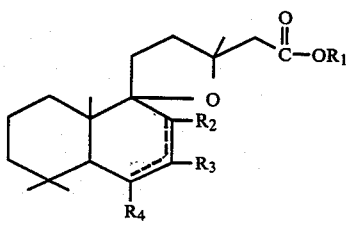

wherein
$R_1$ is H, lower alkyl group or polyhydric alcohol
$R_2$ is lower alkyl group, $-CH_2OCH_3$; $-CH_2OH$;

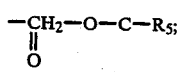

$R_3$ is H, $-OH$;
$R_4$ is H, $=O$ or H, OH
$R_5$ is lower alkyl group and the dashed lines indicate the location of a single or double bond.

Other preferred compounds of the invention have the general formula:

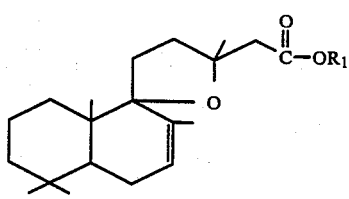

wherein $R_1$ is H, lower alkyl group, or polyhydric alcohol.

Still other preferred compounds of the invention have the general formula:

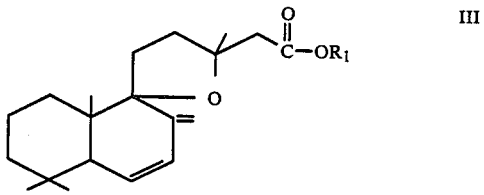

wherein $R_1$ is H, lower alkyl group, glycerol or pentaerythritol.

DETAILED DESCRIPTION OF THE INVENTION

Flowering *Grindelia camporum* plants are used in accordance with the present invention to form hydrogenated grindelia acids and their methyl esters. Especially preferred are the methyl, glycerol, and pentaerythritol esters. The biomass of the flowering *Grindelia camporum* plants are dried and then shredded. The shredded biomass is extracted with organic solvents, such as diethyl ether, to yield a dark resin. The resin contains about 20% neutrals and about 80% acid functionalized structures. The neutrals may, optionally, be separated from the acid structures by partitioning between an aqueous base and a diethyl ether. The separated acid salts are then acidified and separated. The resulting acids are then converted to their methyl esters by any one of a wide variety of standard methods. Exemplary standard methods may include treatment with methyl iodide and potassium carbonate; or treatment with alcohol using dilute acid as the catalyst. The methyl ester mixture is then vacuum distilled at 2 mm Hg. About 70% of the methyl ester mixture is distilled between 190° C. and 250° C. This distillate is light yellow viscous liquid. The methyl esters are present in the light yellow viscous liquid.

The light yellow viscous liquid containing the esters of the original diterpenoid acids is mixed with an equal weight of acetic acid and then is hydrogenated to remove olefinic unsaturation. The hydrogenation takes place in the presence of a 3% by weight of the mixture of a platinum oxide catalyst. The temperature during hydrogenation ranges from 20° C. at the start to 80° C. at the finish for removal of greater than 90% of unsaturation. High percentages of unsaturation may be removed by increasing the temperature and/or pressure of hydrogenation.

The methyl ester mixture is then saponified with ethanolic potassium hydroxide and the hydrogenated diterpenoid acids are recovered. The acid number of the acid mixture is 161.9 meq KOH/g.

The pentaerythritol and glycerol esters are prepared by heating the polyol with the acid. Two equivalents of acid are added per mole of glycerol and four equivalents of acid are added per mole of pentaerythritol. The esters are heated under a stream of nitrogen with stirring for four hours at 190° C. and continuing heating for two hours at 260° C. The pentaerythritol ester so formed has an acid number of 14 meq KOH/g, while the glycerol ester has an acid number of 11 meq KOH/g.

Those skilled in the art will understand and appreciate that other ester functionalized groups may be applied to the resin ring structure and exhibit similar effects on both thermal stability and tack of the resin.

The hydrogenated diterpene acids of *Grindelia camporum* have improved color and thermal stability. The improved oxidative stability is exemplified by the methyl esters of the resin acids and the hydrogenated resin acids. The temperature at which oxidation begins for each of these products is higher than that of the unsaturated resin acids methyl ester. The onset of oxidation for unsaturated resin acids methyl ester is 134.8° C., as determined by differential scanning calorimeter under an atmosphere of oxygen at 350 psig. The onset of oxidation for saturated methyl esters under the same conditions was 160° C.

A similar comparison for the pentaerythritol and glycerol esters is not practical because of the thermal instability of the unsaturated acids, which made preparation of the esters by direct esterification very difficult. However, the pentaerythritol ester of hydrogenated Grindelia acid resin has an onset of oxidation temperature of 171.5° C. and the glycerol ester of the hydrogenated acids has an onset of oxidation temperature of 156.5° C. These onset of oxidation temperatures are higher than the onset of oxidation temperatures for most commercial rosin esters. Thus, the compounds of the present invention have an oxidative stability which is superior to the oxidative stability of most commercial rosin esters. Like rosin esters, the novel compounds of the present invention are useful as adhesives tackifiers.

The hydrogenated diterpene acids differ strikingly in properties from the original diterpene acids available from *Grindelia camporum*. The original diterpene acids are thermally unstable at 190° C., developing color and losing acid functionality. The hydrogenated acid mixture is heated to 180° C. for four hours without significant color development or loss of acid functionality. The unsaturated acids are sensitive to base, thus, saponification of the unsaturated methyl ester yields a highly colored acid mixture. The hydrogenated acid mixture has a Gardner color of 3+. Because of the thermal instability of the unsaturated diterpene acids from *Grindelia camporum*, their esters must be prepared at temperatures which are low, resulting in long reaction times. The hydrogenated diterpene acids permit higher temperatures for esterification, so that complete esterification can be effected in a few hours at 250° C.

If, however, the reaction is carried out in the presence of dilute acid or at high temperature in the presence of a catalyst, double bond migration to $C_7$-$C_8$ causes opening of the tetrahydrofuran ring of the resin. Opening of the thetrahydrofuran ring lowers both the softening point and tack of the hydrogenated and esterified resin.

The hydrogenated and esterified resin of the invention includes tackifier compounds of improved thermal stability of the general formulas I, II and III.

Preferred compounds of the invention have the general formula:

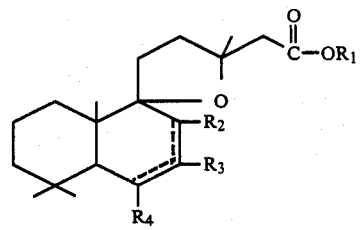

wherein $R_1$ is H, lower alkyl group having about 1 to 8 carbon atom or polyhydric alcohol;

$R_2$ is lower alkyl group having about 1 to 8 carbon atoms, —$CH_2OCH_3$; —$CH_2OH$;

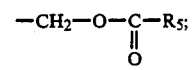

$R_3$ is H, —OH;

$R_4$ is H, =O $R_5$ is lower alkyl group having about 1 to 8 carbon atoms, and the dashed lines indicated the location of a single or double bond.

Other preferred compounds of the invention have the general formula:

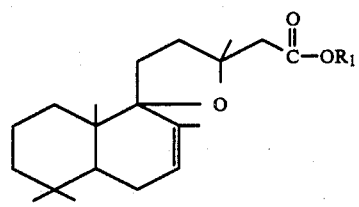

wherein $R_1$ is H, lower alkyl group having about 1 to 8 carbon atoms, or polyhydric alcohol.

Still other preferred compounds of the invention have the general formula:

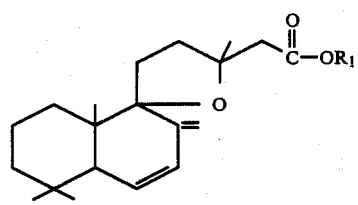

wherein $R_1$ is H, lower alkyl group having about 1 to 8 carbon atoms, glycerol or pentaerythritol.

More preferred diterpene compounds of the invention are the compounds of general formula I where $R_5$ is —$CH_3$, —$CH_2CH_3$,

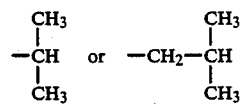

Most preferred diterpene compounds of general formula I are

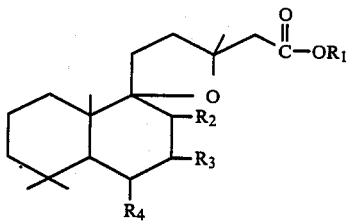

wherein
R₁ is H, lower alkyl group or polyhydric alcohol;
R₂ is lower alkyl group, —CH₂OCH₃; —CH₂OH;

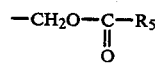

R₃ is H, —OH;
R₄ is H, =O or H, OH;
R₅ is lower alkyl group.

Most preferred diterpene compounds of general formula I are those wherein R₁ is hydrogen, lower alkyl group (from 1 to 8 carbons), glycerol or pentaerythritol, and R₃ and R₄ are H.

Most preferred diterpene compounds of general formula I are those wherein R₁ is hydrogen, lower alkyl group (from 1 to 8 carbons), R₂ is CH₃ and R₃ and R₄ are H.

A naturally occuring methyl ketone derivitive of the resin having the general formula:

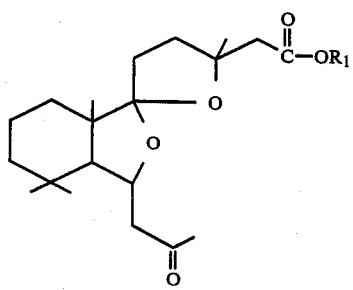

has been isolated and verified by NMR and mass spectroscopy. It has been found that the addition of small concentrations of the methyl ketone ester has a positive effect on both tack and temperature stability when added to the compounds of general formulas I, II and III.

Finally, in the presence of oxygen exposure, the acid compounds of general formula III spontaneously generate a C₇-C₈ epoxide of the general formula:

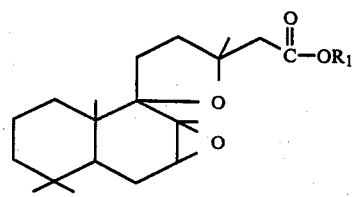

whose esters have been noted to have a positive effect on both tack and temperature stability.

Other features, advantages and specific embodiments of this invention will become readily apparent to those exercising ordinary skill in the art after reading the foregoing disclosures. In this regard, while specific embodiments of this invention have been described in considerable detail, variations and modifications of these embodiments can be effected without departing from the spirit and scope of the invention as disclosed and claimed.

What is claimed is:

1. A compound of the general formula:

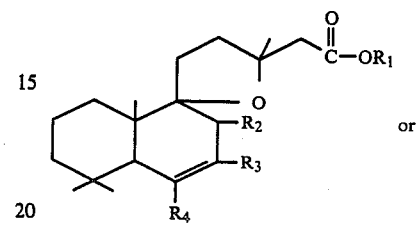 or

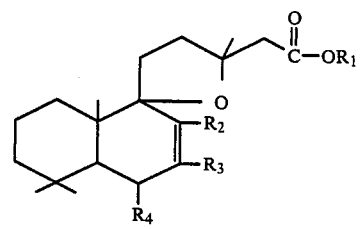

wherein R₁ is a branched or straight chain lower alkyl group having more than one carbon atom, or polyhydric aalcohol residue;
R₂ is lower alkyl group, —CH₂OCH₃; —CH₂OH; —CH₂—O—C—R₅;
R₃ is H, —OH;
R₄ is H, =O or H, OH;
R₅ is lower alkyl group.

2. The compound of claim 1 wherein R₅ is —CH₃, —CH₂CH₃,

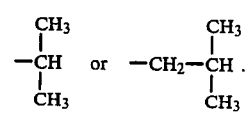

3. The compound of claim 1 wherein R₁ is methyl.
4. The compound of claim 1 wherein R₂ is methyl.
5. The compound of claim 1 wherein the tetrahydrofuran ring (THF) is open as indicated:

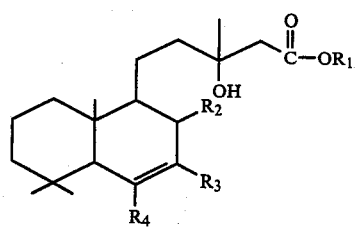

or

-continued

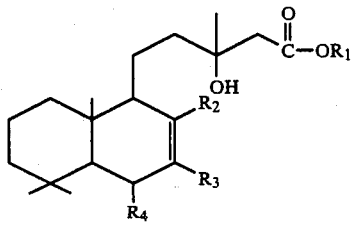

or

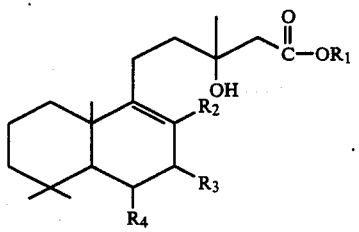

6. The compound of claim 1 wherein said compound is selected from the group consisting of:

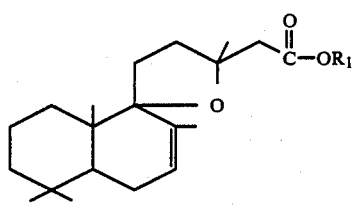

and

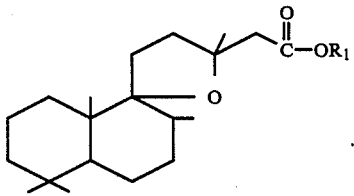

7. The compound of claim 1 wherein said compound is

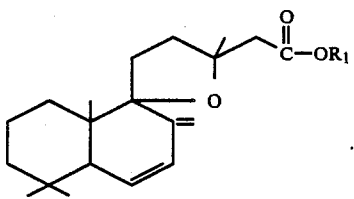

8. The compound of claim 1 wherein said compound is selected from the group consisting of:

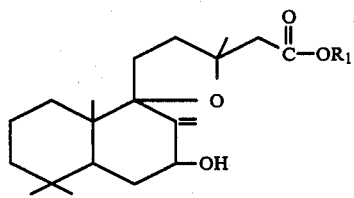

and

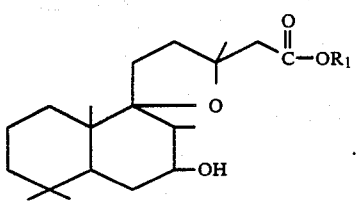

9. The compound of claim 1 wherein said compound is selected from the group consisting of:

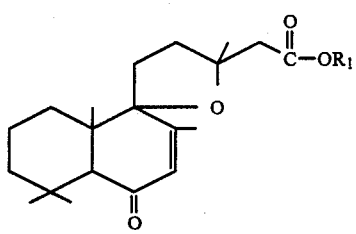

and

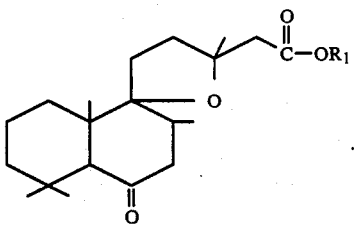

10. The compound of claim 1 wherein said compound is selected from the group consisting of:

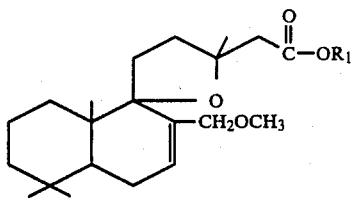

and

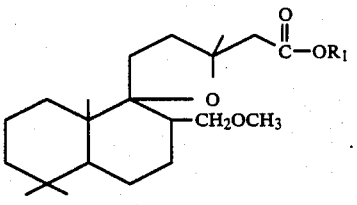

11. The compound of claim 1 wherein said compound is selected from the group consisting of:

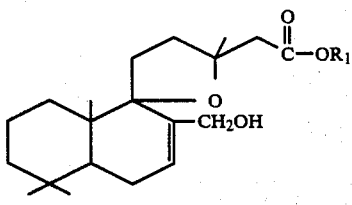

-continued
and

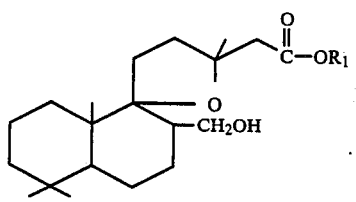

12. The compound of claim 1 wherein said polyhydric alcohol is glycerol or pentaerythritol.

13. The compound of claim 2 wherein said compound is selected from the group consisting of:

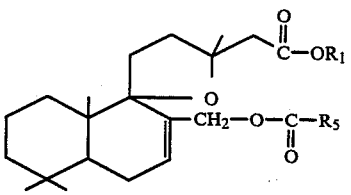

and

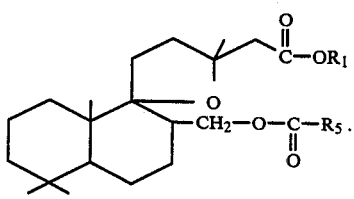

14. The compound of the general formula:

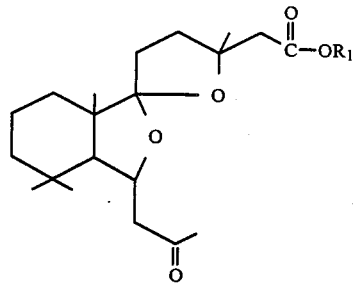

wherein $R_1$ is a lower alkyl group having greater than one carbon atom or polyhydric alcohol residue.

15. The compound of claim 14 wherein $R_1$ is methyl.

16. The compound of claim 14 wherein $R_1$ is glycerol or pentaerythritol.

17. The compound of the general formula:

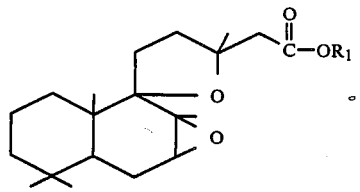

wherein $R_1$ is a lower alkyl group having greater than one carbon atom, glycerol or pentaerythritol residue.

18. The compound of claim 17 wherein $R_1$ is methyl.

19. A resin composition produced by the process, comprising:
separating resin from dry biomass of Grindelia camporum; and
esterifying said resin to form esterified resin of improved oxidative stability.

20. The resin composition produced by the process of claim 19 further comprising:
hydrogenating said esterified resin to form hydrogenated resin of improved thermal stability.

* * * * *